(12) United States Patent
Bouaboula et al.

(10) Patent No.: US 12,427,142 B2
(45) Date of Patent: Sep. 30, 2025

(54) COMBINATION COMPRISING ALPELISIB AND 6-(2,4-DICHLOROPHENYL)-5-[4-[(3S)-1-(3-FLUOROPROPYL)PYRROLIDIN-3-YL [OXYPHENYL]-8,9-DIHYDRO-7H-BENZO[7] ANNULENE-2-CARBOXYLIC ACID

(71) Applicant: Sanofi, Paris (FR)

(72) Inventors: Monsif Bouaboula, Belmont, MA (US); Zhuyan Guo, Belmont, MA (US); Stéphane Poirier, Stoneham, MA (US); Maysoun Shomali, Belmont, MA (US); Fangxian Sun, Melrose, MA (US)

(73) Assignee: Sanofi, Paris (FR)

( * ) Notice: Subject to any disclaimer, the term of this patent is extended or adjusted under 35 U.S.C. 154(b) by 483 days.

(21) Appl. No.: 17/802,223

(22) PCT Filed: Feb. 26, 2021

(86) PCT No.: PCT/EP2021/054815
§ 371 (c)(1),
(2) Date: Aug. 25, 2022

(87) PCT Pub. No.: WO2021/170793
PCT Pub. Date: Sep. 2, 2021

(65) Prior Publication Data
US 2023/0089371 A1    Mar. 23, 2023

(30) Foreign Application Priority Data
Feb. 27, 2020  (EP) ................... 20305190

(51) Int. Cl.
*A61K 31/4439* (2006.01)
*A61K 31/40* (2006.01)
*A61P 35/00* (2006.01)

(52) U.S. Cl.
CPC .......... *A61K 31/4439* (2013.01); *A61K 31/40* (2013.01); *A61P 35/00* (2018.01)

(58) Field of Classification Search
CPC ................ A61K 31/4439; A61K 31/40; A61K 2300/00; A61P 35/00; A61P 35/04
See application file for complete search history.

(56) References Cited

U.S. PATENT DOCUMENTS

| | | |
|---|---|---|
| 6,495,607 B2 | 12/2002 | Bohlmann et al. |
| 7,429,681 B2 | 9/2008 | Pinney et al. |
| 7,612,114 B2 | 11/2009 | Hamaoka et al. |
| 7,799,824 B2 | 9/2010 | Lagu et al. |
| 8,299,112 B2 | 10/2012 | Smith et al. |
| 9,309,211 B2 | 4/2016 | Xiao et al. |
| 9,540,361 B2 | 1/2017 | Dijcks et al. |
| 9,714,221 B1 | 7/2017 | Bouaboula et al. |
| 9,845,291 B2 | 12/2017 | Liang et al. |
| 10,570,090 B2 | 2/2020 | Bouaboula et al. |
| 10,966,963 B2 | 4/2021 | Labadie et al. |
| 11,149,031 B2 | 10/2021 | Bouaboula et al. |
| 11,214,541 B2 | 1/2022 | Bouaboula et al. |
| 11,260,057 B2 | 3/2022 | Bouaboula et al. |
| 11,713,296 B2 | 8/2023 | Malpart et al. |
| 12,157,721 B2 | 12/2024 | Rabion et al. |
| 2012/0130219 A1 | 5/2012 | Zhao et al. |
| 2013/0252890 A1 | 9/2013 | Wintermantel et al. |
| 2015/0080438 A1 | 3/2015 | Wintermantel et al. |
| 2015/0157606 A1 | 6/2015 | Maneval et al. |
| 2016/0184311 A1 | 6/2016 | Chen et al. |
| 2017/0197915 A9* | 7/2017 | Liang .................. C07D 417/12 |
| 2017/0233340 A1* | 8/2017 | Bouaboula ........... C07D 207/12 514/63 |
| 2018/0153828 A1 | 6/2018 | Garner et al. |
| 2019/0167652 A1 | 6/2019 | Abrams et al. |
| 2020/0155521 A1 | 5/2020 | Schwartz et al. |
| 2020/0352905 A1 | 11/2020 | Cartot-Cotton et al. |
| 2020/0361918 A1 | 11/2020 | Bouaboula et al. |
| 2020/0392081 A1 | 12/2020 | Bouaboula et al. |
| 2021/0188771 A1 | 6/2021 | Rabion et al. |
| 2021/0188772 A1 | 6/2021 | Malpart et al. |
| 2022/0073460 A1 | 3/2022 | Bouaboula et al. |
| 2022/0204488 A1 | 6/2022 | Bouaboula et al. |
| 2022/0362248 A1 | 11/2022 | Bouaboula et al. |
| 2023/0028566 A1 | 1/2023 | Billot et al. |
| 2023/0115865 A1 | 4/2023 | Boisnard et al. |
| 2023/0382854 A1 | 11/2023 | Bernardelli et al. |
| 2023/0404971 A1 | 12/2023 | Bouaboula et al. |
| 2024/0091194 A1 | 3/2024 | Cartot-Cotton et al. |

(Continued)

FOREIGN PATENT DOCUMENTS

| | | |
|---|---|---|
| CN | 1309635 A | 8/2001 |
| CN | 106924210 A | 7/2017 |

(Continued)

OTHER PUBLICATIONS

Bernardelli, P., et al., Pending U.S. Appl. No. 18/032,500, filed Apr. 18, 2023.
Bernardelli, P., et al., Pending U.S. Appl. No. 18/032,502, filed Apr. 18, 2023.
Chandarlapaty, S., et al., "277MO SAR439859, an oral selective estrogen receptor (ER) degrader (SERD), in ER + HER2-metastatic breast cancer (mBC): Biomarker analyses from a phase I/II study", Annals of Oncology, vol. 31, No. S4, Sep. 1, 2020, p. S351.
International Search Report for International Application No. PCT/EP2021/078883, mailed Dec. 9, 2021.
International Search Report for International Application No. PCT/EP2021/078916, mailed Dec. 9, 2021.
International Search Report for International Application No. PCT/EP2021/082583, mailed Feb. 25, 2022.

(Continued)

*Primary Examiner* — Amanda L. Aguirre
(74) *Attorney, Agent, or Firm* — McNeill PLLC

(57) ABSTRACT

Herein are provided a combination of alpelisib and of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid or a pharmaceutically acceptable salt thereof, a pharmaceutical composition containing such a combination, and the therapeutic uses thereof, in particular for the treatment of cancer, including breast cancer.

19 Claims, 4 Drawing Sheets

(56) References Cited

U.S. PATENT DOCUMENTS

| | | |
|---|---|---|
| 2024/0101512 A1 | 3/2024 | Bernardelli et al. |
| 2024/0197692 A1 | 6/2024 | Bouaboula et al. |
| 2024/0197739 A1 | 6/2024 | Bouaboula et al. |

FOREIGN PATENT DOCUMENTS

| | | | | |
|---|---|---|---|---|
| CN | 109896991 A | 6/2019 | | |
| EA | 023947 B1 | 7/2016 | | |
| EP | 1229036 A1 | 8/2002 | | |
| EP | 3434272 A1 | 1/2019 | | |
| JP | 2002520388 A | 7/2002 | | |
| JP | 2005528320 A | 9/2005 | | |
| JP | 2008512348 A | 4/2008 | | |
| JP | 2008546706 A | 12/2008 | | |
| JP | 2011500538 A | 1/2011 | | |
| JP | 2013530973 A | 8/2013 | | |
| JP | 2015500814 A | 1/2015 | | |
| JP | 2018537406 A | 12/2018 | | |
| WO | 1992015579 A1 | 9/1992 | | |
| WO | 2000003979 A1 | 1/2000 | | |
| WO | 2003016270 A2 | 2/2003 | | |
| WO | 2003091239 A1 | 11/2003 | | |
| WO | 2004058682 A1 | 7/2004 | | |
| WO | 2006012135 A1 | 2/2006 | | |
| WO | 2006138427 A2 | 12/2006 | | |
| WO | 2009047343 A1 | 4/2009 | | |
| WO | 2009101634 A2 | 8/2009 | | |
| WO | 2012037410 A2 | 3/2012 | | |
| WO | 2012037411 A2 | 3/2012 | | |
| WO | 2012068284 A2 | 5/2012 | | |
| WO | 2013097773 A1 | 7/2013 | | |
| WO | 2015028409 A1 | 3/2015 | | |
| WO | 2016051374 A1 | 4/2016 | | |
| WO | 2016097071 A1 | 6/2016 | | |
| WO | 2016097072 A1 | 6/2016 | | |
| WO | 2016176666 A1 | 11/2016 | | |
| WO | 2017140669 A1 | 8/2017 | | |
| WO | 2018091153 A1 | 5/2018 | | |
| WO | 2019020559 A1 | 1/2019 | | |
| WO | 2019106604 A1 | 6/2019 | | |
| WO | 2020014435 A1 | 1/2020 | | |
| WO | 2020049153 A1 | 3/2020 | | |
| WO | 2020112765 A1 | 6/2020 | | |
| WO | 2020225375 A1 | 11/2020 | | |
| WO | WO-2021127043 A1 * | 6/2021 | ........... | A61K 31/366 |
| WO | WO-2021178846 A1 * | 9/2021 | ............ | A61K 31/00 |
| WO | 2022084280 A1 | 4/2022 | | |
| WO | 2022084298 A1 | 4/2022 | | |
| WO | 2022106711 A1 | 5/2022 | | |
| WO | 2022218956 A1 | 10/2022 | | |
| WO | 2022218958 A1 | 10/2022 | | |

OTHER PUBLICATIONS

Ashizawa, Kazuhide, "Optimization of salt and crystalline forms, and crystallization techniques," Pharm Tech Japan, 2002, vol. 18, No. 10, pp. 81-96 (machine translation of excerpts).

Hirayama, Noriaki, "Handbook for organic compounds crystal preparation," 2008, pp. 17-23, 37-40, 45-51, 57-65 (machine translation of excerpts).

Rabion, A., et al., Pending U.S. Appl. No. 18/924,400, filed Oct. 23, 2024.

Anstead, Gregory, M. et al., "2,3-Diarylindenes and 2,3-Diarylindenones: Synthesis, Molecular Structure, Photochemistry, Estrogen Receptor Binding Activity, and Comparisons with Related Triarylethylenes", Journal of Medicinal Chemistry, vol. 31, No. 7, pp. 1316-1326 (1988).

Bardia, A., et al., Dose-escalation study of SAR439859, an oral selective estrogen receptor (ER) degrader (SERD), in postmenopausal women with ER+/HER2− metastatic breast cancer (mBC), Journal of Clinical Oncology, vol. 37, Suppl. 15, p. 1054 (May 20, 2019).

Billot, P. et al., Pending U.S. Appl. No. 17/783,364, filed Jun. 8, 2022.

Boinsard, S., et al., Pending U.S. Appl. No. 17/765,169, filed Mar. 30, 2022.

Bouaboula, M., et al., Pending U.S. Appl. No. 16/634,089, filed Jan. 24, 2020. (Issued).

Bouaboula, M., et al., Pending U.S. Appl. No. 17/460,629, filed Aug. 30, 2021.

Bouaboula, M., et al., Pending U.S. Appl. No. 17/532,051, filed Nov. 22, 2021.

Bouaboula, M., et al., Pending U.S. Appl. No. 17/579,187, filed Jan. 19, 2022.

Bouaboula, M., et al., U.S. Appl. No. 16/414,558, filed May 16, 2019. (Issued).

Bouaboula, M., et al., U.S. Appl. No. 17/124,852, filed Dec. 17, 2020. (Issued).

Campone, M., et al., "Abstract P5-11-02: Dose-escalation study of SAR439859, an oral selective estrogen receptor degrader, in postmenopausal women with estrogen receptor-positive and human epidermal growth factor receptor 2—negative metastatic breast cancer," Cancer Research, vol. 80, Suppl. 4, pp. 1-4 (Feb. 2020).

Cartot-Cotton, S., et al., Pending U.S. Appl. No. 16/870,031, filed May 8, 2020.

Deroo, B.J., et al., "Estrogen Receptors and Human Disease", The Journal of Clinical Investigation, vol. 116, No. 3, pp. 561-570 (2006).

El-Ahmad, Y., et al., "Discovery of 6-(2,4-Dichlorophenyl)-5-[4-[(3S)-1-(3-fluoropropyl)-pyrrolidin-3-yl]-oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," Journal of Medicinal Chemistry, vol. 63, No. 2, pp. 512-528 (2019).

Extended European Search Report issued in European Application No. 19305593.6 on Oct. 30, 2019, 7 pages.

Franks, et al., "Selective Estrogen Receptor Modulators: Cannabinoid Receptor Inverse Agonists with Differential CB1 and CB2 Selectively," Frontiers in Pharmacology, vol. 7, No. 503, pp. 1-16 (2016).

Golub et al., "Molecular Classification of Cancer: Class Discovery and Class Prediction by Gene Expression Monitoring", Science, Oct. 15, 1999, vol. 286, pp. 531-537.

Gould, P. "Salt selection for basic drugs," International Journal of Pharmaceutics, vol. 33, pp. 201-217 (1986).

International Search Report for International Application No. PCT/EP2017/053282, mailed Jul. 6, 2017.

International Search Report for International Application No. PCT/EP2017/068446, mailed Sep. 12, 2017.

International Search Report for International Application No. PCT/EP2018/069901, mailed Oct. 12, 2018.

International Search Report for International Application No. PCT/EP2019/073823, mailed Oct. 10, 2019.

International Search Report for International Application No. PCT/EP2019/073827, mailed Oct. 9, 2019.

International Search Report for International Application No. PCT/EP2020/062743, mailed Aug. 10, 2020.

International Search Report for International Application No. PCT/EP2020/085011, mailed Jan. 25, 2021.

International Search Report for International Application No. PCT/EP2021/054815, mailed May 12, 2021.

Jordan, Craig V., "Antiestrogens and Selective Estrogen Receptor Modulators as Multifunctional Medicines. 1. Receptor Interactions," Journal of Medicinal Chemistry, vol. 46, No. 6, pp. 883-908 (2003).

Lala, P.K., et al., "Role of Nitric Oxide in Tumor Progression: Lessons From Experimental Tumors", Cancer Metastasis Reviews, Mar. 1998, vol. 17, No. 1, pp. 91-106.

Malpart, J., et al., Pending U.S. Appl. No. 17/193,776, filed Mar. 5, 2021.

Mannava, M.K.C., et al., "Enhanced Bioavailability in the Oxalate Salt of the Antituberculosis Drug Ethionamide," Crystal Growth & Design, vol. 16(3), pp. 1591-1598, (2016).

McCague, Raymond et al., "Nonisomerizable Analogues of (Z)- and (E)-4-Hydroxytamoxifen. Synthesis and Endocrinological Proper-

(56) References Cited

OTHER PUBLICATIONS ties of Substituted Diphenylbenzocycloheptenes", Journal of Medicinal Chemistry, vol. 31, No. 7, pp. 1285-1290 (1988).
Miller, Chris P., "SERMs: Evolutionary Chemistry, Revolutionary Biology," Current Pharmaceutical Design, vol. 8, No. 23, pp. 2089-2111 (2002).
Pickar, et al., "SERMs: Progress and future perspectives," Maturitas, Elsevier, Vo. 67, pp. 129-138 (2010).
Rabion, A., et al., Pending U.S. Appl. No. 17/193,706, filed Mar. 5, 2021.
RN 1861739-57-2, Registry Database Compound, 2016.
Ruff, et al., "Estrogen Receptor Transcription and Transactivation Structure-Function Relationship in DNA- and Ligand-Binding Domains of Estrogen Receptors", Breast Cancer Research, 2000, vol. 2, No. 5, pp. 353-359.
Translation of Office Action issued in Japanese Application No. 2018-515615, mailed on Sep. 18, 2018, 3 pages.
Translation of Search Report issued in Chinese Application No. 201780023008.0, mailed Apr. 23, 2020, 3 pages.
Ullrich et al., "Estrogen receptor modulator review," Expert Opinion, 16(5): 559-572, 2006.
Bouaboula, M. et al., Pending U.S. Appl. No. 18/037,949, filed May 19, 2023.
Cancer [online]—Medline Plus, [Retrieved on Jul. 6, 2007] Retrieved from the Internet, URL: http://www.nlm.nih.gov/medlineplus/cancer.html, pp. 1-10.
Anonymous, "Phase 1 / 2 Study of Amcenestrant (SAR439859) Single Agent and in Combination With Other Anti-cancer Therapies in Postmenopausal Women With Estrogen Receptor Positive Advanced Breast Cancer," Sep. 15, 2017, URL: https://www.clinicaltrials.gov/ct2/show/NCT03284957.
Besret, et al., "Translational strategy using multiple nuclear imaging biomarkers to evaluate target engagement and early therapeutic efficacy of SAR439859, a novel selective estrogen receptor degrader", Ejnmmi Research, Biomed Central Ltd, London, UK, vol. 10, No. 1, Jun. 29, 2020, pp. 1-13.
Bouaboula, M., et al., Pending U.S. Appl. No. 18/286,496, filed Oct. 11, 2023.
Bouaboula, M., et al., Pending U.S. Appl. No. 18/286,510, filed Oct. 11, 2023.
International Search Report for International Application No. PCT/EP2022/059700, mailed Jul. 8, 2022.
International Search Report for International Application No. PCT/EP2022/059704, mailed Jul. 21, 2022.
Robinson, Dan, R. et al., "Activating ESR1 mutations in hormone-resistant metastatic breast cancer", Nat. Genet., Dec. 2013, 45(12), 1446-1451.
Toy, Weiyi, et al., "Activating ESR1 mutations differentially impact the efficacy of ER antagonists", Cancer Discovery, Mar. 2017, 7(3), 277-287.
Littke, A.F., et al., "Versatile Catalysts for the Suzuki Cross-Coupling of Arylboronic Acids with Aryl and Vinyl Halides and Triflates under Mild Conditions," Journal of the American Chemical Society, 122(17): 4020-4028 (2000).
André, F., et al., Alpelisib for PIK3CA-Mutated, Hormone Receptor-Positive Advanced Breast Cancer, The New England Journal of Medicine, vol. 380, No. 20, May 16, 2019, 12 pages (1929-1940).

\* cited by examiner

COMBINATION COMPRISING ALPELISIB AND 6-(2,4-DICHLOROPHENYL)-5-[4-[(3S)-1-(3-FLUOROPROPYL)PYRROLIDIN-3-YL[OXYPHENYL]-8,9-DIHYDRO-7H-BENZO[7]ANNULENE-2-CARBOXYLIC ACID

CROSS-REFERENCE TO RELATED APPLICATIONS

This application is a national phase entry pursuant to 35 U.S.C. § 371 of International Application No. PCT/EP2021/054815, filed Feb. 26, 2021, which claims the benefit of priority to European Application No. 20305190.9, filed Feb. 27, 2020, the contents of each of which are incorporated by reference herein in their entirety for any purpose.

Herein are provided a combination of alpelisib and of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, a pharmaceutical composition containing such combination, and the therapeutic uses of such combination and pharmaceutical composition, in particular for the treatment of cancer.

The estrogen receptor α (ESR1) is expressed in the majority of breast tumors, enabling them to respond to the mitogenic actions of estrogens.

6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, hereafter designated as "compound (1)", is a selective estrogen receptor degrader (SERD) which is an estrogen receptor antagonist and accelerates the proteasomal degradation of the estrogen receptor. This compound is disclosed in the patent application PCT/EP2017/053282, published as WO 2017/140669:

Compound (1)

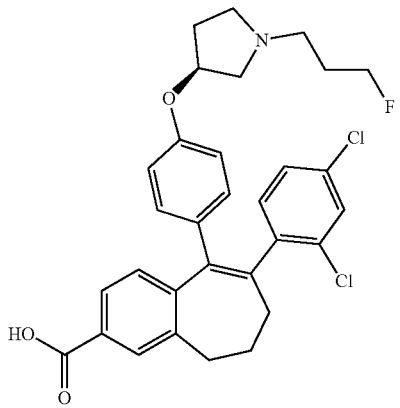

Alpelisib, also known as (2S)—N¹-{4-methyl-5-[1-(1,1,1-trifluoro-2-methylpropan-2-yl)pyridin4-yl]-1,3-thiazol-2-yl}pyrrolidine-1,2-dicarboxamide, is an alpha-specific PI3K inhibitor, with the following formula:

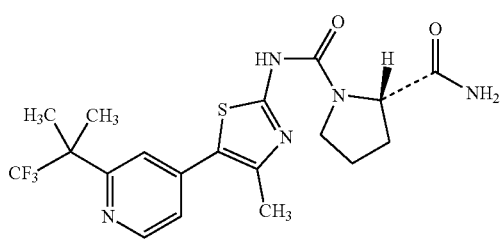 [SMILES: Cc1nc(NC(=O)N2CCC[C@H]2C(N)=O)sc1-c1ccnc(C(C)(C)C(F)(F)F)c1]

Alpelisib is marketed under the tradename PIQRAY® and is indicated, in combination with the endocrine therapy fulvestrant, for the treatment of breast cancer in postmenopausal women, and in men, with hormone receptor (HR)-positive, human epidermal growth factor receptor 2 (HER2)-negative, PIK3CA-mutated, advanced or metastatic breast cancer following progression on or after an endocrine-based regimen (FDA label).

There is always a need to find new antitumoral treatments. Now, it is shown herein that a combination of compound (1) with alpelisib is well tolerated, demonstrates significant anti-tumor efficacy and induces tumor stasis or regression, with a synergistic effect compared to each of the active ingredient alone.

Herein is provided a combination comprising compound (1) and alpelisib.

In the combination provided herein, compound (1) may exist not only in the form of a zwitterion (i.e. a globally neutral molecule having an acid group and a basic group), but also in the form of addition salts with acids or bases. Such addition salts may be used in the above combination. Hence, herein is provided a combination comprising compound (1), or a pharmaceutically acceptable salt thereof, and alpelisib.

In an embodiment, the combination of compound (1), or a pharmaceutically acceptable salt thereof, with alpelisib shows therapeutic synergy. A combination demonstrates therapeutic synergy if its therapeutic effect is superior compared to the cumulative effect of either active agent of the combination alone.

In another embodiment, compound (1), or a pharmaceutically acceptable salt thereof, and alpelisib are administered by the oral route.

Provided herein is also a combination of compound (1), or a pharmaceutically acceptable salt thereof, and alpelisib for its use as a medicament.

Provided herein is also a pharmaceutical composition comprising compound (1), or a pharmaceutically acceptable salt thereof, and alpelisib, as well as at least one pharmaceutically acceptable excipient.

The excipients are selected from the customary excipients which are known to a person skilled in the art. More particularly, the excipients are selected from those useful for oral administration in whatever form (liquid solution, dispersion or suspension, tablets, capsules or the like).

In another embodiment, compound (1), or a pharmaceutically acceptable salt thereof, and alpelisib may be administered simultaneously, separately, or spaced out over a period of time (sequential administration). Therefore, the combination and pharmaceutical composition provided herein are not exclusively limited to the ones which are obtained by physical association of the constituents in a single unit dosage, but also to those which allow a separate administration, which can be simultaneous or sequential (also called "spaced out", or "spread out") over a period of time.

Herein is also provided a pharmaceutical kit which comprises:

(i) a first pharmaceutical composition comprising compound (1), or a pharmaceutically acceptable salt thereof, and at least one pharmaceutically acceptable excipient;

(ii) a second pharmaceutical composition comprising alpelisib, and at least one pharmaceutically acceptable excipient;

wherein the first pharmaceutical composition and the second pharmaceutical composition are in separate compartments and are intended to be independently administered, each administration with regards to the other one being simultaneous or spaced out (sequential) over time.

In the combinations, pharmaceutical compositions and pharmaceutical kit described above, the compound (1) or pharmaceutically acceptable salt thereof and alpelisib are advantageously present at effective doses, adapted considering the treated pathology and the condition of the patient to which it is administered. In particular, for alpelisib the recommended dose for cancer treatment for adult patients is 300 mg (two 150 mg tablets) taken orally once daily, with food.

Herein is also provided a combination comprising compound (1), or a pharmaceutically acceptable salt thereof, and alpelisib, as well as a pharmaceutical composition and kit as described above, for use in the treatment of cancer.

Herein is also provided compound (1) or a pharmaceutically acceptable salt thereof for use in the treatment of cancer by co-administration with alpelisib.

Herein is also provided alpelisib for use in the treatment of cancer by co-administration with compound (1) or a pharmaceutically acceptable salt thereof.

Co-administration is understood herein as an administration of the active ingredients to a patient in need thereof, which is separated, simultaneous or spaced out (sequential) over time, in respect of each of the active ingredient.

In some embodiments, compound (1) or a pharmaceutically acceptable salt thereof and alpelisib are administered in a therapeutically effective amount. A "therapeutically effective amount" means the amount of an active ingredient or combination of active ingredients that, when administered to a patient for treating a disease, is sufficient to affect such treatment for the disease. The "therapeutically effective amount" will vary depending on the disease and its severity and the age, weight, etc . . . , of the mammal to be treated.

In some embodiments, compound (1) or a pharmaceutically acceptable salt thereof and alpelisib are administered in an amount to show therapeutic synergy.

In another embodiment, the cancer is a hormone dependent cancer.

In another embodiment, the cancer is an estrogen receptor dependent cancer, particularly the cancer is an estrogen receptor a dependent cancer.

In another embodiment, the cancer is resistant to anti-hormonal treatment.

In another embodiment, the cancer is a cancer with wild type estrogen receptors.

In another embodiment, the cancer is a cancer with deregulated function of estrogen receptors related to, but not limited to, at least one epigenetic and genetic alteration of estrogen receptors such as mutation, amplification, splice variant.

In another embodiment, the cancer is a cancer with mutated estrogen receptors.

In another embodiment, the mutations of estrogen receptors can include, but not limited to, new or known mutations such as Leu536Arg, Tyr537Ser, Tyr537Asn, or Asp538Gly.

In another embodiment, the cancer is an estrogen-sensitive cancer.

In another embodiment, the cancer is breast cancer, more particularly an estrogen receptor positive breast cancer (ERα positive breast cancer), or a metastasis thereof, such as a cerebral metastasis.

Herein is also provided a method of treating the pathological conditions indicated above, particularly breast cancer, comprising administering to a subject in need thereof a therapeutically effective amount of compound (1), or a pharmaceutically acceptable salt thereof, and a therapeutically effective amount of alpelisib.

Herein is also provided a method of treating the pathological conditions indicated above, particularly breast cancer, comprising administering to a subject in need thereof a pharmaceutical composition or a pharmaceutical kit as described above.

Herein is also provided a method of treating the pathological conditions indicated above, particularly breast cancer, comprising administering to a subject in need thereof a combination as described above.

Herein is also provided a method of treating the pathological conditions indicated above, particularly breast cancer, comprising co-administering to a subject in need thereof compound (1) or a pharmaceutically acceptable salt thereof and alpelisib. In said method, compound (1) or a pharmaceutically acceptable salt thereof is administered with alpelisib either simultaneously or spaced out over time.

Herein is also provided a method of treating the pathological conditions indicated above, particularly breast cancer, comprising co-administering to a subject in need thereof alpelisib and compound (1) or a pharmaceutically acceptable salt thereof. In said method, alpelisib is administered with compound (1), or a pharmaceutically acceptable salt thereof, either simultaneously or spaced out over time.

In an embodiment of the methods described above, the subject is a human.

Herein is also provided a combination comprising compound (1), or a pharmaceutically acceptable salt thereof, and alpelisib for the manufacture of a medicament useful in treating the pathological conditions indicated above, particularly breast cancer.

Herein is also provided the use of compound (1), or a pharmaceutically acceptable salt thereof, in the manufacture of a medicament useful in treating the pathological conditions indicated above, particularly breast cancer, by co-administration with alpelisib.

Herein is also provided the use of alpelisib in the manufacture of a medicament useful in treating the pathological conditions indicated above, particularly breast cancer, by co-administration with compound (1) or a pharmaceutically acceptable salt thereof.

Herein is also provided an article of manufacture, a packaging, or an administration unit, comprising:

a packaging material;

the above defined combination, pharmaceutical composition, or pharmaceutical kit; and a label or package insert contained within said packaging material, indicating that said combination, pharmaceutical composition or pharmaceutical kit is administered to a patient for the treatment of cancer.

The examples below show the pharmacological results obtained with compound (1), alpelisib and their combination against a breast cancer cell line xenograft in mice.

EVALUATION OF THE EFFICACY OF 6-(2,4-DICHLOROPHENYL)-5-[4-[(3S)-1-(3-FLUORO-PROPYL) PYRROLIDIN-3-YL]OXYPHENYL]-8, 9-DIHYDRO-7H-BENZO[7]ANNULENE-2-CARBOXYLIC ACID COMBINED WITH ALPELISIB AGAINST A SUBCUTANEOUS BREAST CANCER CELL LINE XENOGRAFT IN FEMALE NUDE MICE

1: Experiment 1

In the present study, the anti-tumor efficacy of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid ("compound (1)"), combined with alpha-specific phosphoinositide 3-kinase (PI3K) inhibitor alpelisib, was investigated after 22 day treatment against a subcutaneous MCF7-Y537S human breast cancer cell line xenograft in female nude mice.

The treated groups included compound (1) at 20 mg/kg alone, alpelisib at 25 mg/kg alone, and the combination of compound (1) and alpelisib at the same dose and regime.

Compound (1) was orally dosed twice a day (BID) and alpelisib was orally dosed once a day (QD) for 22 days. Anti-tumor efficacy was evaluated by tumor volume measurement.

1-1: Experimental Procedure
1-1-1: Animals, Cell Line, Compounds

Female BALB/c nude mice were obtained from Shanghai Sino-British SIPPR/BK Laboratory Animal Co., LTD (Shanghai, CHINA). Animals were allowed to acclimate for at least four days before the study enrollment. Mice were 6 to 8 weeks old and weighed between 18 and 24 grams at the beginning of the treatments. These animals were housed under conditions outlined in the guidelines approved by the Institutional Animal Care and Use Committee (IACUC) of WuXi AppTec following the guidance of the Association for Assessment and Accreditation of Laboratory Animal Care (AAALAC).

Parental MCF7 cells were obtained from the American Type Culture Collection (ATCC® HTB-22™). MCF7-Y537S (ESR1) cell line was MCF7 cells expressing the ER.Y537S variant that was generated by Sanofi Biology Discovery Group. Y537S mutation was introduced in ESR1 construct (GenBank NM_000125.3) by site directed mutagenesis (Toy W. et al., Cancer Discovery, 2017, 7, 277-287). The construct was transfected in MCF7 cells which were selected for their growth in absence of estradiol. MCF-Y537S is an ESR1 mutation that confers estrogen-independent activity to ERα (Estrogen Receptor alpha) and contributes to endocrine resistant disease (Robinson D. R. et al., Nat Genet., 2013, 45 (12), 1446-1451). The cells were grown in Eagle's Minimum Essential Medium (EMEM) supplemented with 10% fetal bovine serum (FBS), human Insulin, in 5% $CO_2$ at 37° C. The cells were harvested in 0.25% Trypsin EDTA and washed by Phosphate Buffered Saline (PBS) and re-suspended in PBS with 75% Matrigel. The cells ($20\times10^6$ cells/per mouse) were subcutaneously (SC) implanted into the right flank of female nude mice.

When the MCF7-Y537S tumors were established, the tumors were reserved as tumor stocks for fragment implantation. The tumors were serially propagated through fragment tissue transplantation subcutaneously. The fragment tumor tissues were subcutaneously implanted into the right flank of female nude mice. 28 mice were assigned in this experiment.

Alpelisib (commercially available, marketed under the tradename PIQRAY®) was formulated in 100% of HPMC (hydroxypropyl-methylcellulose)/TWEEN80 0.5/0.1% in water. Compound (1) was prepared in 5% Solutol HS15 (purchased from Sigma) at pH 3.0.

Dose volume for compound (1) and alpelisib for oral administration: 10 ml/kg by oral gavage.

Doses: compound (1) at 20 mg/kg and alpelisib at 25 mg/kg in the above volume.

1-1-2: Study Design, End Points

The animals required for experiment (plus extra) were pooled and implanted with MCF7-Y537S tumor fragment tissues. On day 0 (20 days post implantation), the mice were pooled and randomly distributed to the treatment and control groups (7 mice per group), where median tumor volumes for each group was 173 mm³. Treatments of compound (1) and alpelisib were initiated on day 0. Compound (1) was orally administered at 20 mg/kg BID (8 hours apart) and alpelisib was orally administered at 25 mg/kg QD, for 22 days. Animal body weight was assessed daily.

The dosages are expressed in mg/kg and based on daily body weight per animal. Vehicle treated animals were used as controls. Mice were checked daily for adverse clinical reactions. Individual mice were weighed daily until the end of the experiment. Mice would be euthanized when morbid or weight loss ≥20% was observed. Tumors were measured with a caliper twice weekly until final sacrifice. When a tumor size reached approximately 2000 mm³ or when there are animal health issues (40% area of a tumor ulcerated), animals would be euthanized, and date of death recorded. Solid tumor volumes were estimated from two-dimensional tumor measurements and calculated according to the following equation:

$$\text{Tumor volume (mm}^3) = \frac{\text{length (mm)} \times \text{width}^2 \text{ (mm}^2)}{2}$$

Toxicity End Points:

A dosage producing either 15% body weight loss during 3 consecutive days for an individual mouse, 20% body weight loss during 1 day, or 10% or more drug related deaths, was considered an excessively toxic dosage, unless under certain circumstances bodyweight loss or animal death can be considered non-drug related. Examples include animal handling issues such as misgavage, tumor model related issues such as tumor induced cachexia leading to body weight loss that can be observed in control or vehicle treated groups and excessive tumor ulceration. Mice that have non-drug related death or significant bodyweight loss will not be considered toxic and will be excluded from statistical analysis. Animal body weight included the tumor weight.

Efficacy End Points:

The primary efficacy end points include tumor volume changes from baseline summarized by the ratio of medians of tumor volume changes from baseline between the treated and control groups (ΔT/ΔC). Changes in tumor volume for each treated (T) and control (C) group are calculated for each animal on each day by subtracting the tumor volume on the day of first treatment (staging day) from the tumor volume on the specified observation day. The median ΔT is calculated for the treated group and the median ΔC is calculated for the control group. The ratio ΔT/ΔC is calculated and expressed as percentage:

$$\Delta T/\Delta C = \left(\frac{\text{Median } deltaT}{\text{Median } deltaC}\right) \times 100$$

ΔT/ΔC≤40% is considered as therapeutically active, ΔT/ΔC=0% is considered as tumor stasis, and ΔT/ΔC<0% is considered as tumor regression (very active). ΔT/ΔC>40% is considered as therapeutically inactive.

Percent tumor regression is defined as % (percentage) of tumor volume decrease in the treated group on a specified observation day compared to its volume when the study was initiated. At a specific timepoint (t) and for each animal, the regression percentage is calculated using the following formula:

$$\% \text{ regression (at } t) = \left(\frac{\text{volume}_{t0} - \text{volume}_t}{\text{volume}_{t0}}\right) \times 100$$

The median percent regression for a group on a given day is then calculated by taking the median of individual % regression values calculated for each animal in the group. The day of calculation is determined by the day when ΔT/ΔC is calculated, except if median percent regression is not representative of the activity of the group. In this case, the day is determined by the first day when the median percent regression is maximal.

1-1-3: Statistical Analysis

A two-way analysis of variance (ANOVA) with factors treatment and day (repeated) is performed on tumor volume changes from baseline. It is followed by contrast analyses with Bonferroni-Holm correction for multiplicity to compare all treated groups to the control group and to compare the combination versus each single agent at the dose involved in the combination at each day from day 0 to 22.

In the figures, the medians and Median Absolute Deviation (MAD) of each group are represented for each day of measurement.

In the tables, the medians and Normalized MAD (nMAD=1.4826*MAD) of each group are reported for each day of measurement.

Tumor volume changes from baseline are calculated for each animal and each day by subtracting the tumor volume on the day of first treatment (day 0) from the tumor volume on the specified observation day.

All statistical analyses were performed using SAS version 9.2 software. A probability of less than 5% (p<0.05) was considered as significant.

1-2: Results

Compound (1) at 20 mg/kg BID, alpelisib 25 mg/kg QD and the combination of compound (1) and alpelisib at the doses and regime for 22 days were well tolerated and no significant body weight loss was observed in the study.

Compound (1) at a dose of 20 mg/kg BID for 22 days had no statistically significant anti-tumor effect on tumor growth with ΔT/ΔC value of 47% (p=0.9411) on day 22. Alpelisib at a dose of 25 mg/kg QD for 22 days did not induce statistically significant anti-tumor efficacy either with ΔT/ΔC value of 46% (p=0.3593) on day 22. When compound (1) at 20 mg/kg combined with alpelisib 25 mg/kg with the same dose regime as BID for compound (1) and QD for alpelisib, the combination treatment demonstrated statistically significant anti-tumor efficacy (tumor stasis) with ΔT/ΔC value of 3% (p<0.0001) on day 22. The statistical analysis indicated the combination effect was significantly different when compared to either compound (1) alone or alpelisib alone on day 22 (p<0.0001).

Detailed results are shown in Tables 1 to 3 below, as well as in FIGS. 1 and 2.

Figure 1:
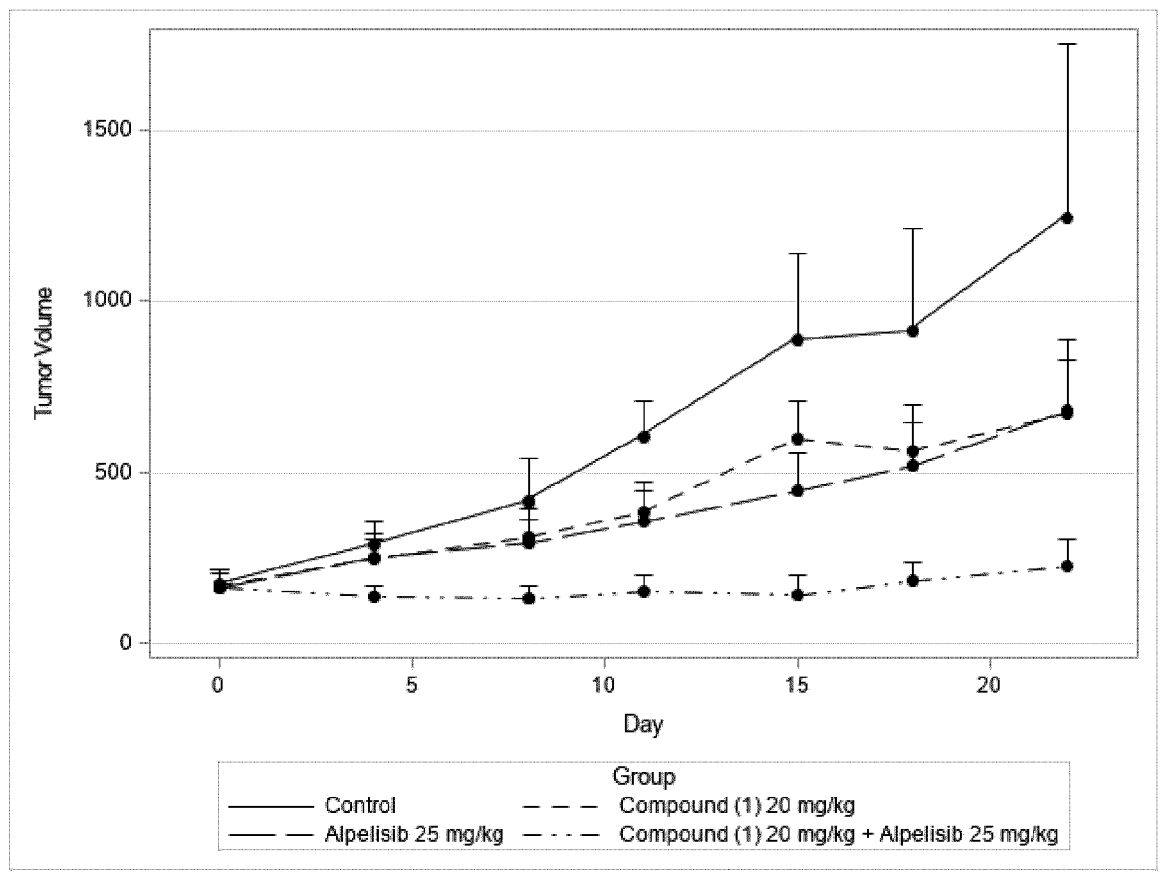
FIG. 1: Antitumor activity of compound (1) combined with alpelisib against subcutaneous human breast cancer cell line MCF7-Y537S xenograft in nude mice according to experiment 1: tumor volume evolution. The curves represent medians + or − MAD (Median Absolute Deviation) at each day for each group.
Figure 2:
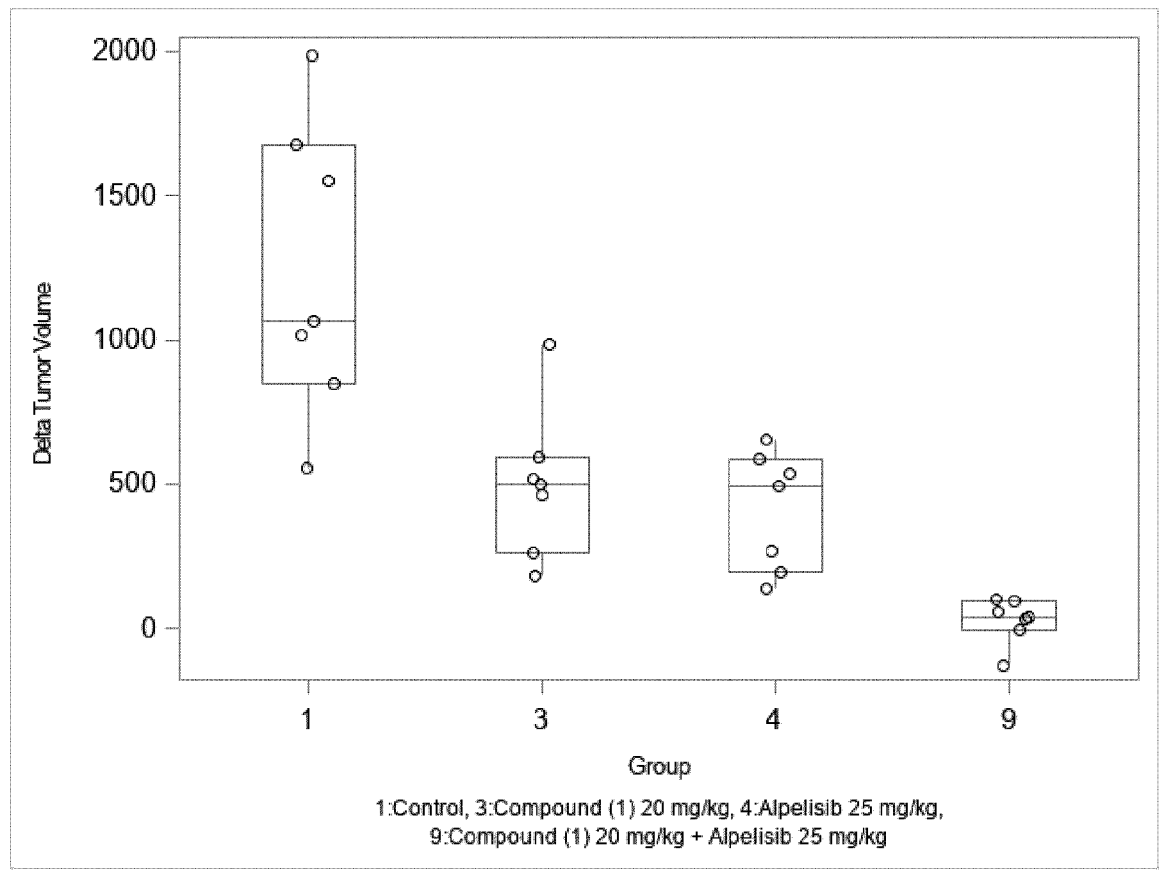
FIG. 2: Antitumor activity of compound (1) combined with alpelisib against subcutaneous human breast cancer cell line MCF7-Y537S xenograft in nude mice according to experiment 1: tumor volume changes from baseline on day 22. Points represent individual tumor volume changes from baseline on day 22; bars correspond to medians.

From this experiment, we conclude that compound (1) at 20 mg/kg twice a day combined with the PI3K inhibitor alpelisib at 25 mg/kg once a day in MCF7-Y537S human breast cancer cell line xenograft model in nude mice induced significant anti-tumor efficacy that was superior to single agents alone, and induced tumor growth inhibition and tumor stasis.

TABLE 1

Efficacy of compound (1) combined with alpelisib against subcutaneous MCF7-Y537S human breast cancer xenograft in nude mice, according to experiment 1.
PO: per os

| Agent | Route/ Dosage (in mL/kg per injection) | Dosage in mg/kg per injection | Schedule in days (total of 22 days) | Un-scheduled death (Day of death) | ΔT/ΔC in % at day 22 | Median % of regressions on day 22 | Regressions Partial | Regressions Complete | p-value on day 22 | Biological Interpretation |
|---|---|---|---|---|---|---|---|---|---|---|
| Vehicle | PO, BID (10) | — | — | 0/7 | 100 | — | 0/7 | 0/7 | — | — |
| Compound (1) | PO, BID (10) | 20 | 0 to 22 | 0/7 | 47 | 0 | 0/7 | 0/7 | p = 0.9411 | Inactive |
| Alpelisib | PO, QD (10) | 25 | 0 to 22 | 0/7 | 46 | 0 | 0/7 | 0/7 | p = 0.3593 | Inactive |
| Compound (1) + Alpelisib | PO, BID (10) PO, QD (10) | 20 + 25 | 0 to 22 | 0/7 | 3 | 0 | 0/7 | 0/7 | p < 0.0001 | Active |

TABLE 2

Efficacy of compound (1) combined with alpelisib against subcutaneous human breast cancer cell line MCF7-Y537S xenograft model in nude mice, according to experiment 1. Comparison of each group to the control group at each day.
Tumor volume changes from baseline mm$^3$: Median (nMAD)*, n and p-value#

| Treatment Group | Global | Day 4 | Day 8 | Day 11 | Day 15 | Day 18 | Day 22 |
|---|---|---|---|---|---|---|---|
| Control | — | 87.0 (25.20) n = 7 | 237.0 (105.26) n = 7 | 430.0 (75.61) n = 7 | 713.0 (272.80) n = 7 | 738.0 (382.51) n = 7 | 1065.0 (717.58) n = 7 |
| Compound (1) 20 mg/kg | — 0.2279 | 43.0 (51.89) n = 7 0.5181 | 121.0 (45.96) n = 7 0.2234 | 214.0 (69.68) n = 7 0.1776 | 360.0 (220.91) n = 7 0.3604 | 392.0 (100.82) n = 7 0.4047 | 501.0 (131.95) n = 7 0.9411 |
| Alpelisib 25 mg/kg | — 0.0425 | 68.0 (50.41) n = 7 0.4176 | 102.0 (57.82) n = 7 0.0417 | 163.0 (103.78) n = 7 0.0103 | 262.0 (124.54) n = 7 0.0410 | 315.0 (145.29) n = 7 0.1006 | 491.0 (241.66) n = 7 0.3593 |
| Compound (1) 20 mg/kg + Alpelisib 25 mg/kg | — <0.0001 | −23.0 (26.69) n = 7 0.0001 | −4.0 (14.83) n = 7 <0.0001 | 24.0 (28.17) n = 7 <0.0001 | 30.0 (26.69) n = 7 <0.0001 | 41.0 (48.93) n = 7 <0.0001 | 37.0 (60.79) n = 7 <0.0001 | p-values obtained with a contrast analysis versus control at each day with Bonferroni-Holm adjustment for multiplicity after a two-way ANOVA on tumor volume changes from baseline.
*MAD = Median Absolute Deviation; nMAD = normalized MAD; nMAD = 1.4826*MAD.
For the combination compound (1) at 20 mg/kg + Alpelisib at 25 mg/kg, the effect on tumor volume changes from baseline is significant compared to the control group from day 4 to day 22.
n = number of animals.

TABLE 3

Efficacy of compound (1) combined with alpelisib against subcutaneous human breast cancer cell line MCF7-Y537S xenograft model in nude mice, according to experiment 1. Comparison of compound (1) 20 mg/kg and alpelisib 25 mg/kg as single agents versus the combination at each day.
Tumor volume changes from baseline mm$^3$: Median (nMAD)*, n and p-value#

| Treatment Group | Global | Day 4 | Day 8 | Day 11 | Day 15 | Day 18 | Day 22 |
|---|---|---|---|---|---|---|---|
| Compound (1) 20 mg/kg + Alpelisib 25 mg/kg | — | −23.0 (26.69) n = 7 | −4.0 (14.83) n = 7 | 24.0 (28.17) n = 7 | 30.0 (26.69) n = 7 | 41.0 (48.93) n = 7 | 37.01 (60.79) n = 7 |
| Alpelisib 25 mg/kg | — <.0001 | 68.0 (50.41) n = 7 0.0802 | 102.0 (57.82) n = 7 0.0009 | 163.0 (103.78) n = 7 0.0002 | 262.0 (124.54) n = 7 <.0001 | 315.0 (145.29) n = 7 <.0001 | 491.0 (241.66) n = 7 <.0001 |
| Compound (1) 20 mg/kg | — <.0001 | 43.0 (51.89) n = 7 0.0465 | 121.0 (45.96) n = 7 <.0001 | 214.0 (69.68) n = 7 <.0001 | 360.0 (220.91) n = 7 <.0001 | 392.0 (100.82) n = 7 <.0001 | 501.0 (131.95) n = 7 <.0001 | p-values obtained with a contrast analysis to compare the combinations of compound (1) and alpelisib versus each single agent at the dose involved in the combination at each day with Bonferroni-Holm adjustment for multiplicity after a two-way ANOVA on tumor volume changes from baseline.
*MAD = Median Absolute Deviation; nMAD = normalized MAD; nMAD = 1.4826*MAD
The effect of the combination of compound (1) at 20 mg/kg + alpelisib at 25 mg/kg is significantly greater than the effect of alpelisib at 25 mg/kg alone on day 4 to day 22.
The effect of the combination of compound (1) at 20 mg/kg + alpelisib at 25 mg/kg is significantly greater than the effect of compound (1) at 20 mg/kg alone on day 4 to day 22.
n = number of animals.

2: Experiment 2

A second experiment in mice was performed, under the same protocol as in experiment 1 described above and with the same endpoints, albeit the following differences.

Each mouse was inoculated subcutaneously in the right flank region with MCF7-Sanofi tumor cells (2×10$^7$) in 0.25 ml of PBS/Matrigel (1:1) mixture for tumor development. 32 mice were assigned in this experiment.

Compound (1) was prepared in 20% Solutol HS15 (purchased from Sigma) at pH 3.5.

Female BALB/c nude mice were obtained from Vital River Laboratories Research Models and Services (Beijing, China). These animals were housed under conditions outlined in the guidelines approved by the Institutional Animal Care and Use Committee (IACUC) of Crown Bioscience Inc. (Beijing) following the guidance of the Association for Assessment and Accreditation of Laboratory Animal Care (AAALAC).

The animals required for experiment (plus extra) were pooled and implanted with MCF7-Y537S tumor cells. On day 0 (40 days post implantation), the mice were pooled and randomly distributed to the treatment and control groups (8 mice per group), where median tumor volumes for each group was 201 mm$^3$. Compound (1) was orally administered at 10 mg/kg BID (8 hours apart) and alpelisib was orally administered at 25 mg/kg QD, for 28 days. Animal body weight was assessed daily.

The results were as follows.

Compound (1) at 10 mg/kg BID, alpelisib 25 mg/kg QD and the combination of compound (1) and alpelisib at the doses and regime for 28 days were well tolerated and no significant body weight loss was observed in the study.

Compound (1) at a dose of 10 mg/kg BID for 28 days had statistically significant anti-tumor effect on tumor growth with $\Delta T/\Delta C$ value of 37% ($p<0.0001$) on day 28. Alpelisib at a dose of 25 mg/kg QD for 28 days induced statistically significant anti-tumor efficacy with $\Delta T/\Delta C$ value of 66% ($p=0.0271$) on day 28. When compound (1) at 10 mg/kg combined with alpelisib 25 mg/kg with the same dose regime as BID for compound (1) and QD for alpelisib, the combination treatment demonstrated statistically significant anti-tumor efficacy (tumor regression) with $\Delta T/\Delta C$ value of $-16\%$ ($p<0.0001$) on day 28. The statistical analysis indicated the combination effect was significantly different when compared to either compound (1) alone or alpelisib alone on day 28 ($p<0.0001$).

Detailed results are shown in Tables 4 to 6 below, as well as in FIGS. 3 and 4.

BRIEF DESCRIPTION OF THE DRAWINGS

Figure 3:
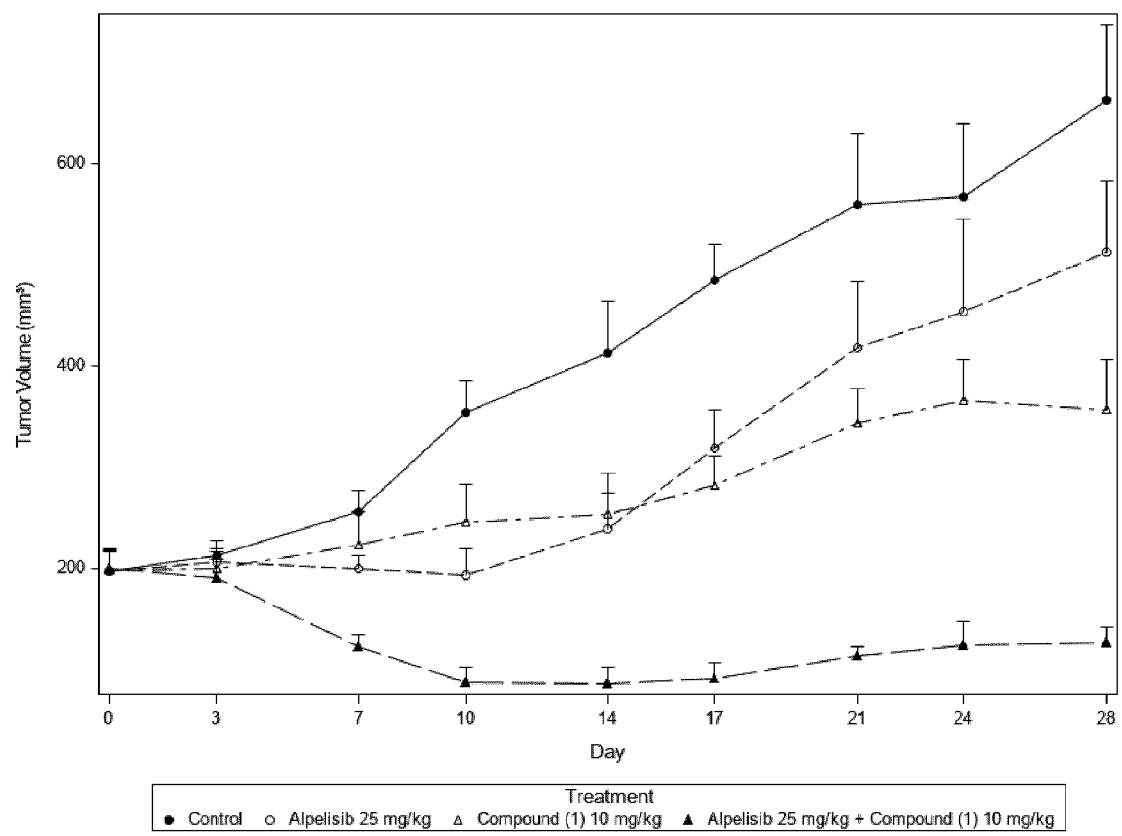

FIG. 3: Antitumor activity of compound (1) combined with alpelisib against subcutaneous human breast cancer cell line MCF7-Y537S xenograft in nude mice according to experiment 2: tumor volume evolution. The curves represent medians + or − MAD (Median Absolute Deviation) at each day for each group.

Figure 4:
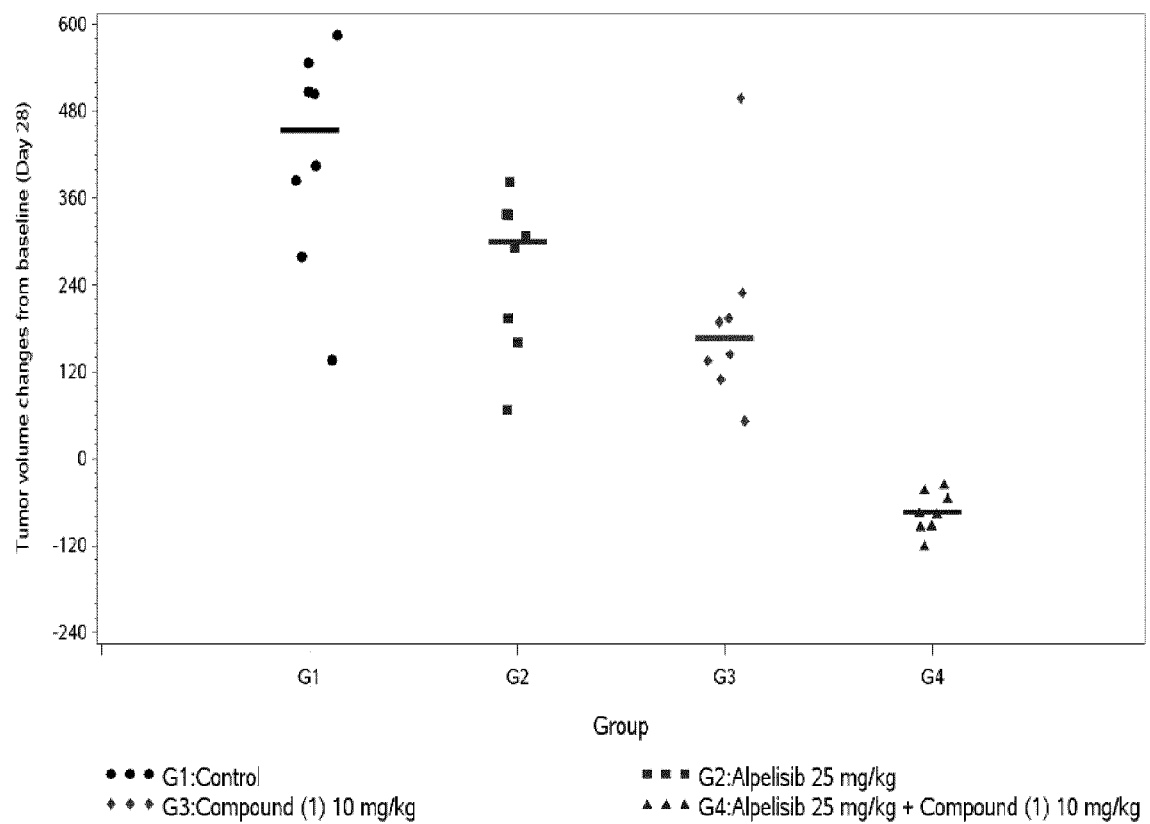

FIG. 4: Antitumor activity of compound (1) combined with alpelisib against subcutaneous human breast cancer cell line MCF7-Y537S xenograft in nude mice according to experiment 2: tumor volume changes from baseline on day 28. Points represent individual tumor volume changes from baseline on day 28, bars correspond to medians.

From experiment 2, we conclude that compound (1) at 10 mg/kg twice a day combined with the PI3K inhibitor alpelisib at 25 mg/kg once a day in MCF7-Y537S human breast cancer cell line xenograft model in nude mice induced significant anti-tumor efficacy that was superior to single agents alone, and induced tumor regression.

TABLE 4

Efficacy of compound (1) combined with alpelisib against subcutaneous MCF7-Y537S human breast cancer xenograft in nude mice, according to experiment 2.
PO: per os

| Agent | Route/ Dosage (in mL/kg per injection) | Dosage in mg/kg per injection | Schedule in days (total of 28 days) | Unscheduled death (Day of death) | $\Delta T/\Delta C$ in % at day 28 | Median % of regressions on day 28 | Regressions Partial | Regressions Complete | p-value on day 28 | Biological Interpretation |
|---|---|---|---|---|---|---|---|---|---|---|
| Vehicle | PO, BID (10) | — | — | 0/8 | 100 | — | 0/8 | 0/8 | — | — |
| Compound (1) | PO, BID (10) | 10 | 0 to 28 | 0/8 | 37 | 0 | 0/8 | 0/8 | p < 0.0001 | active |
| Alpelisib | PO, QD (10) | 25 | 0 to 28 | 0/8 | 66 | 0 | 0/8 | 0/8 | p = 0.0271 | inactive |
| Compound (1) + Alpelisib | PO, BID (10) PO, QD (10) | 10 + 25 | 0 to 28 | 0/8 | <0 | −16 | 8/8 | 0/8 | p < 0.0001 | very active |

TABLE 5

Efficacy of compound (1) combined with alpelisib against subcutaneous human breast cancer cell line MCF7-Y537S xenograft model in nude mice, according to experiment 2. Comparison of each group to the control group at each day.
Tumor volume changes from baseline $mm^3$: Median (nMAD), n and p-value

| Treatment Group | Global | Day 3 | Day 7 | Day 10 | Day 14 | Day 17 | Day 21 | Day 24 | Day 28 |
|---|---|---|---|---|---|---|---|---|---|
| Control | — | 14.5 (19.27) n = 8 | 59.0 (14.83) n = 8 | 152.0 (22.24) n = 8 | 223.0 (68.20) n = 8 | 286.5 (66.72) n = 8 | 351.5 (111.20) n = 8 | 359.5 (112.68) n = 8 | 454.5 (120.83) n = 8 |
| Alpelisib 25 mg/kg | — | 7.0 (9.64) n = 8 | −9.0 (23.72) n = 8 | −17.0 (11.86) n = 8 | 44.0 (36.32) n = 8 | 121.5 (30.39) n = 8 | 211.0 (80.80) n = 8 | 245.5 (106.75) n = 8 | 299.5 (89.70) n = 8 |
| | <0.0001 | 0.4727 | <0.0001 | <0.0001 | <0.0001 | <0.0001 | 0.0099 | 0.0267 | 0.0271 |
| Compound (1) 10 mg/kg | — | 9.0 (8.90) n = 8 | 36.0 (42.25) n = 8 | 48.0 (29.65) n = 8 | 62.5 (34.10) n = 8 | 92.0 (35.58) n = 8 | 167.5 (63.75) n = 8 | 189.5 (59.30) n = 8 | 166.5 (65.98) n = 8 |
| | 0.0008 | 0.7484 | 0.5309 | 0.0057 | <0.0001 | <0.0001 | 0.0013 | 0.0095 | <0.0001 |

TABLE 5-continued

Efficacy of compound (1) combined with alpelisib against subcutaneous
human breast cancer cell line MCF7-Y537S xenograft model in nude mice, according to
experiment 2. Comparison of each group to the control group at each day.
Tumor volume changes from baseline mm³: Median (nMAD), n and p-value

| Treatment Group | Global | Day 3 | Day 7 | Day 10 | Day 14 | Day 17 | Day 21 | Day 24 | Day 28 |
|---|---|---|---|---|---|---|---|---|---|
| Compound (1) 10 mg/kg + Alpelisib 25 mg/kg | — | −7.0 (6.67) n = 8 | −89.5 (20.76) n = 8 | −112.0 (17.79) n = 8 | −107.0 (19.27) n = 8 | −102.5 (27.43) n = 8 | −89.0 (23.72) n = 8 | −83.0 (22.98) n = 8 | −74.5 (28.91) n = 8 |
|  | <0.0001 | 0.1764 | <0.0001 | <0.0001 | <0.0001 | <0.0001 | <0.0001 | <0.0001 | <0.0001 | p-values obtained with a contrast analysis versus control at each day with Bonferroni-Holm adjustment for multiplicity after a two-way ANOVA on tumor volume changes from baseline.
*MAD = Median Absolute Deviation; nMAD = normalized MAD; nMAD = 1.4826*MAD
For the combination compound (1) at 10 mg/kg + alpelisib at 25 mg/kg, the effect on tumor volume changes from baseline is significant compared to the control group from day 3 to day 28.
n = number of animals.

TABLE 6

Efficacy of compound (1) combined with alpelisib against subcutaneous
human breast cancer cell line MCF7-Y537S xenograft model in nude mice, according to
experiment 2. Comparison of compound (1) 10 mg/kg and alpelisib 25 mg/kg as single
agents versus the combination at each day.
Tumor volume changes from baseline mm³: Median (nMAD)*, n and p-value#

| Treatment Group | Global | Day 3 | Day 7 | Day 10 | Day 14 | Day 17 | Day 21 | Day 24 | Day 28 |
|---|---|---|---|---|---|---|---|---|---|
| Compound (1) 10 mg/kg + Alpelisib 25 mg/kg | — | −7.0 (6.67) n = 8 | −89.5 (20.76) n = 8 | −112.0 (17.79) n = 8 | −107.0 (19.27) n = 8 | −102.5 (27.43) n = 8 | −89.0 (23.72) n = 8 | −83.0 (22.98) n = 8 | −74.5 (28.91) n = 8 |
| Compound (1) 10 mg/kg | — | 9.0 (8.90) n = 8 | 36.0 (42.25) n = 8 | 48.0 (29.65) n = 8 | 62.5 (34.10) n = 8 | 92.0 (35.58) n = 8 | 167.5 (63.75) n = 8 | 189.5 (59.30) n = 8 | 166.5 (65.98) n = 8 |
|  | <0.0001 | 0.2333 | <0.0001 | <0.0001 | <0.0001 | <0.0001 | <0.0001 | <0.0001 | <0.0001 |
| Alpelisib 25 mg/kg | — | 7.0 (9.64) n = 8 | −9.0 (23.72) n = 8 | −17.0 (11.86) n = 8 | 44.0 (36.32) n = 8 | 121.5 (30.39) n = 8 | 211.0 (80.80) n = 8 | 245.5 (106.75) n = 8 | 299.5 (89.70) n = 8 |
|  | <0.0001 | 0.4804 | 0.0003 | <0.0001 | <0.0001 | <0.0001 | <0.0001 | <0.0001 | <0.0001 | p-values obtained with a contrast analysis to compare the combinations of compound (1) and alpelisib versus each single agent at the dose involved in the combination at each day with Bonferroni-Holm adjustment for multiplicity after a two-way ANOVA on tumor volume changes from baseline.
*MAD = Median Absolute Deviation; nMAD = normalized MAD; nMAD = 1.4826*MAD
The effect of the combination of compound (1) at 10 mg/kg + alpelisib at 25 mg/kg is significantly greater than the effect of alpelisib at 25 mg/kg alone on day 3 to day 28.
The effect of the combination of compound (1) at 10 mg/kg + alpelisib at 25 mg/kg is significantly greater than the effect of compound (1) at 10 mg/kg alone on day 3 to day 28.
n = number of animals.

The invention claimed is:

1. A combination comprising 6-(2,4-dichlorophenyl)-5-[4-[(3S)-1-(3-fluoropropyl)pyrrolidin-3-yl]oxyphenyl]-8,9-dihydro-7H-benzo [7]annulene-2-carboxylic acid, or a pharmaceutically acceptable salt thereof, and alpelisib.

2. The combination according to claim 1, wherein the combination shows therapeutic synergy.

3. The combination according to claim 1, for use in the treatment of cancer.

4. The combination according to claim 3, wherein the cancer is breast cancer.

5. The combination according to claim 1, wherein 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and alpelisib are administered simultaneously or spaced out over a period of time.

6. A pharmaceutical composition comprising 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and alpelisib, and at least one pharmaceutically acceptable excipient.

7. A kit comprising:
(i) a first pharmaceutical composition comprising 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and at least one pharmaceutically acceptable excipient; and
(ii) a second pharmaceutical composition comprising alpelisib, and at least one pharmaceutically acceptable excipient;
wherein the first pharmaceutical composition and the second pharmaceutical composition are in separate compartments.

8. The kit of claim 7, further comprising a label or package insert indicating that the first and second pharmaceutical compositions are administered for the treatment of cancer.

9. The kit of claim 8, wherein the cancer is breast cancer.

10. The kit of claim 7, further comprising a label or package insert indicating that the first and second pharmaceutical compositions are administered simultaneously or sequentially with respect to each other.

11. The kit of claim 7, further comprising a label or package insert indicating that the first and second pharmaceutical compositions are administered simultaneously with respect to each other.

12. The kit of claim 7, further comprising a label or package insert indicating that the first and second pharmaceutical compositions are administered sequentially with respect to each other.

13. A method of treating cancer in a subject in need thereof, the method comprising administering to the subject 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and alpelisib.

14. The method of claim 13, wherein the cancer is breast cancer.

15. The method of claim 13, wherein the 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and alpelisib are administered in amounts that exhibit therapeutic synergy.

16. The method of claim 13, wherein the 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, is administered simultaneously or sequentially with alpelisib.

17. The method of claim 13, wherein the 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, is administered simultaneously with alpelisib.

18. The method of claim 13, wherein the 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, is administered sequentially with alpelisib.

19. The method of claim 13, wherein the subject is a human.

\* \* \* \* \*